(12) United States Patent
Zukic

(10) Patent No.: US 11,265,659 B2
(45) Date of Patent: Mar. 1, 2022

(54) METHOD FOR ENHANCING THE CONFIGURATION OF A HEARING AID DEVICE OF A USER

(71) Applicant: TWO PI GMBH, Vienna (AT)

(72) Inventor: Tarik Zukic, Vienna (AT)

(73) Assignee: TWO PI GmbH, Vienna (AT)

( * ) Notice: Subject to any disclaimer, the term of this patent is extended or adjusted under 35 U.S.C. 154(b) by 0 days.

(21) Appl. No.: 17/045,375

(22) PCT Filed: Apr. 11, 2018

(86) PCT No.: PCT/AT2018/000019
§ 371 (c)(1),
(2) Date: Oct. 5, 2020

(87) PCT Pub. No.: WO2019/195866
PCT Pub. Date: Oct. 17, 2019

(65) Prior Publication Data
US 2021/0160626 A1    May 27, 2021

(51) Int. Cl.
*H04R 25/00* (2006.01)

(52) U.S. Cl.
CPC ......... *H04R 25/43* (2013.01); *H04R 25/505* (2013.01); *H04R 2225/39* (2013.01)

(58) Field of Classification Search
CPC ...................................................... H04R 25/00

USPC ................................................... 381/312, 60
See application file for complete search history.

(56) References Cited

U.S. PATENT DOCUMENTS

| 2008/0001735 | A1* | 1/2008 | Tran | G16H 80/00 |
| | | | | 340/539.22 |
| 2011/0280422 | A1* | 11/2011 | Neumeyer | H04R 25/00 |
| | | | | 381/314 |
| 2014/0193008 | A1 | 7/2014 | Zukic | |
| 2018/0063653 | A1 | 3/2018 | Aschoff | |

FOREIGN PATENT DOCUMENTS

| KR | 2011 0007355 | 1/2011 |
| WO | WO 2014/023340 | 2/2014 |

OTHER PUBLICATIONS

International Search Report and Written Opinion for PCT/AT2018/000019, dated Dec. 12, 2018.

* cited by examiner

*Primary Examiner* — Suhan Ni
(74) *Attorney, Agent, or Firm* — Joseph E. Maenner; Maenner & Associates, LLC

(57) ABSTRACT

The invention relates to a method for enhancing the configuration of a hearing aid device (2) of a user, said method using an external configuration unit (3) accessing a database of previously known user records, wherein the hearing aid device (2) is arranged to be configured according to an individual set of configuration parameters.

12 Claims, 2 Drawing Sheets

METHOD FOR ENHANCING THE CONFIGURATION OF A HEARING AID DEVICE OF A USER

CROSS-REFERENCE TO RELATED APPLICATION

Figure 1:
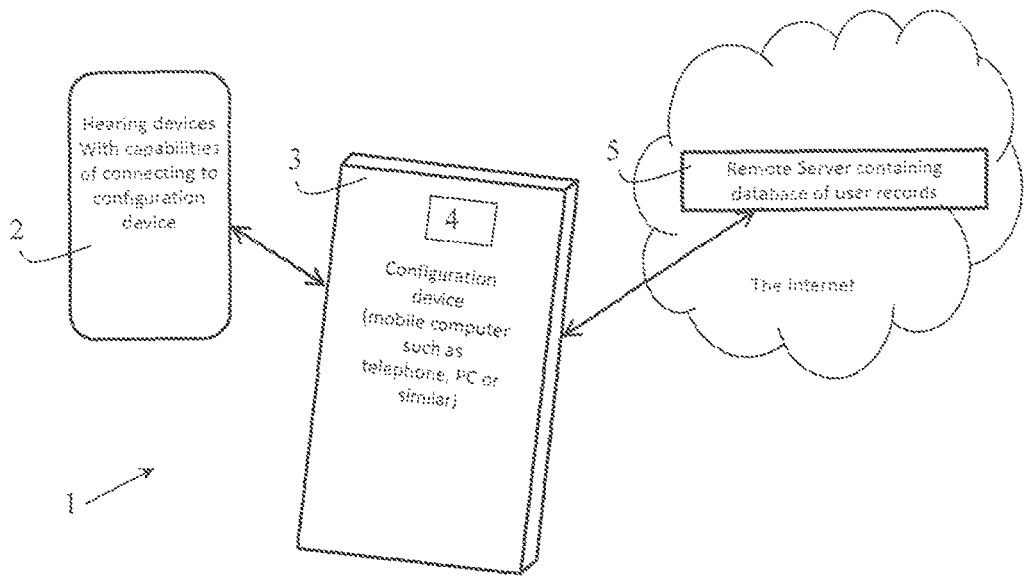

The present application is a 371 of Patent Cooperation Treaty application PCT/AT2018/000019, filed on Apr. 11, 2018, which is incorporated herein by reference in its entirety.

I. FIELD OF THE INVENTION AND DESCRIPTION OF PRIOR ART

The invention relates to a method for enhancing the configuration of a hearing aid device of a user. Moreover, the invention also relates to a hearing aid configuration system for carrying out the method according to the invention.

Invention provides a method that can be used together with the patented invention EP 2 175 669 B1 (two Pi patent "Method and System for configuring a hearing aid device").

Paired Comparisons

Fitting of hearing aids means selecting the parameters of signal processing that will provide optimal benefits for an individual user. The parameters constitute a vector that represents a point in multi-dimensional parameter space. In the process of paired comparisons (sometimes called pair-wise comparisons) preferably two distinct parameter vectors are tested in order to collect user's preference for one of them. Input sound is processed according to each of the parameter vectors producing two output sounds (stimuli) that are presented to the user. The user selects the output sound that he prefers providing so his preference for one of the parameter vectors.

The parameter space is mapped onto a space of psychological value of "individual preference". The iteration of paired comparisons over the entire parameter space can be used to provide psychological ranking of parameter vectors. This method can be used to obtain individually most preferred parameter vector.

Paired comparisons are very-well known method for fitting of hearing aids [Kuk 2002]. However, these comparisons are usually limited as follows:

In traditional paired comparisons, the user was presented with pair of competing sounds in succession and confronted with the question: "Do you prefer the first sound or the second sound". This method not only required a trained professional to guide the user through the process, but involved a demanding auditory cognition task while memorizing sound quality in the working memory. Therefore the user is experiencing a cognitive fatigue after a number of preference decisions and the decisions become less reliable.

An enhanced method and system for in-situ paired comparisons is disclosed in the patent EP 2 175 669 B1 (Two Pi patent: Method and system for configuring a hearing aid device). The self-fit interactive paired comparison proposed there resolves the cognitive difficulties by simultaneously providing test sounds and visually anchoring them to the speakers shown on a screen.

Traditionally, paired comparisons employed strategies such as tournament and round robin to minimize number of stages and at the same time comprehensively cover the whole parameter space [Aml 2009]. But in each case the procedure involved comprehensive search through all possible discrete parameter vectors.

In modern hearing aids, with large number of parameters (dimensions of parameter space), method of paired comparisons faces the difficulty of covering all possible combinations of parameters.

II. SUMMARY OF THE INVENTION

The number of the paired comparisons involved in obtaining the best-fit is the limiting factor and it is an object of the invention to minimize this number while still obtaining the best-fit result and as such to reduce cognitive load involved and produce so reliable decisions. If the method is implemented in a consumer product, reducing the length of the procedure while retaining the validity of the outcome results in a competitive advantage of such product.

This object is achieved by a method according to the invention of the above mentioned kind, said method using an external configuration unit accessing a database of previously known user records, wherein the hearing aid is arranged to be configured according to an individual set of configuration parameters (i.e. user specific (final set is user specific); for instance gain, compression ratio, compression threshold, each parameter adjustable within a certain resolution and for a certain frequency band), said method comprising the following steps:

a) receiving user description data, said description data comprising previously known data about the user, a1) matching the user description data with the database of previously known user records in order to derive user preference description data b) using the user preference description data to derive b1) an assumed set of preferred configuration parameters, and b2) an assumed set of preferred values for the assumed set of preferred configuration parameters, said parameters and its values according to steps b1) and b2) being determined based on an estimation of their likelihood of matching the users preference description data, c) preparing at least two different sound samples based on a pre-defined set of samples and the parameters and its values derived in step b) and presenting the at least two prepared different sound samples to the user, d) receiving a user selection relating the preferred one of the at least two sound samples via the external configuration unit, e) combining the result of the selection into a new user preference description data, said new user preference data being merged with the user preference description data of step b) and iteratively repeating steps b) to e) until a pre-definable success condition is reached, f) yielding a final set of configuration parameters and its values, and g) configuring the hearing aid device according to the final set of configuration parameters and its values.

By virtue of this method a best-fit configuration can be derived quickly and reliably. The pre-definable success condition according to step e) can be based on a comparison with a certain threshold, for instance a limited number of iterations (for instance a maximum of 10 iterations), a limitation of the deviation of the selection results of the user, and/or a limitation of the distance between parameter sets or a combination of these criterions.

In other words, the present invention can be referred to as method and system for in-situ fitting of a hearing aid by paired comparison of pre-processed sounds.

Preferably, one sample is configured according to the assumed preferred configuration parameters and its values according to step b), said sample constituting an assumed preferred sample, and wherein another sample is configured according to similar configuration parameters but different parameter values, constituting a verification sample in order to verify the assumed preferred sample.

Advantageously, precisely two samples are presented in step c).

Preferably, the parameters obtained in step b) are sampled in dependence from their probability density function, wherein their probability destiny function is obtained from the user preference description data. Herein, the term sampling means randomly obtaining multiple parameter values in a way that their frequency of occurrence follows the probability density function.

Advantageously, the parameters in step b) are obtained by applying an amplification-prescription formula, for instance NAL-NL2, to an audiogram with suitable likelihood to match the user preference data. This means that we that parameters like gain and compression ratio are not varied, but the audiogram—parameters like gain and compression ratio are uniquely determinable from audiogram using NAL-NL2 formula.

Preferably, in step b) the assumed set of preferred configuration parameters is split into two groups, namely a first group of configuration parameters to be varied in step c), and a second group of configuration parameters which are set to an assumed default value and remain unvaried among the samples during step c).

Advantageously, the database of previously known user records is locally stored on the external configuration unit.

Preferably, the database of previously known user records is stored on a server and the external configuration unit is configured to connect to this server in order to access to the database.

Advantageously, the database of previously known user records is updated by the external configuration unit once a final set of configuration parameters and its values is determined according to step f), said final parameters and its values being added to the database.

Preferably, the initial set of configuration parameters comprises at least one, preferably at least two or more of the following parameters: {gain; compression ratio; compression threshold, attack-time constant, release-time constant, noise reduction level} for at least one frequency band. Moreover, the initial set of configuration parameters can comprise a number of frequency channels covering a bandwidth ranging from 100 Hz to 10 kHz, said bandwidth being split into the number of frequency channels, wherein the number is at least 3, preferably at least 5, most preferably between 5 and 15 (in particular precisely 12), wherein the configuration parameters of step b), in particular signal processing parameters such as gain or compression ratio, are set for each channel.

Advantageously, the user description data received in step a) comprises at last one of the following parameters: {age; gender; sex; prior configuration data of the hearing aid device of the user and date of prior configuring data of the hearing aid device of the user; user preference data obtained in the prior session; data from diagnostic applications such as audiometric measurement of audiogram}

Preferably, the external configuration unit is a mobile phone, in particular a smart phone.

Advantageously, a pre-defined set of samples according to step c) is stored on the external configuration unit or on a server.

Preferably, in step e) the new user preference description data is inferred from the previous user preference description data and the user selection according to Bayes' rule.

Furthermore, the above mentioned object is solved with a hearing aid configuration system for carrying out the method according to the invention, said system comprising
- at least one hearing aid to be configured,
- at least one external configuration unit for communicating with the at least one hearing aid, and
- at least one computer-readable storage medium (either locally stored on the external configuration unit or on a server) comprising a program logic for carrying out the method according to the invention, wherein said external configuration being configured to access the computer-readable storage medium.

II.1 Further Optional Details of the Invention and Explanations

Generally speaking, the invention can be applied on several distinct uses of paired comparison procedure, for instance:
- first-fit: first time user with no prior diagnostic knowledge about his hearing loss performs the procedure to obtain hearing loss compensation parameters
- fine-tuning: user of a hearing aid that is already fitted, perform the procedure to improve the fitting. The improved fitting can become necessary during acclimatization to a hearing aid
- or due to progress of hearing loss, and
- rehabilitation: user of a hearing aid performs paired comparison procedure to improve his cognitive abilities for speech recognition.

Furthermore, the hearing aid configuration system can comprise:
- Hearing aid (or a pair of hearing aids in case of binaural hearing loss compensation) with means to connecting to control device and exchanging command and audio signals with control device. Audio signals from control device can be played into speakers of hearing aids. Command data from the control device can control signal processing in the hearing aid, change the parameters of signal processing and store permanently the parameters for future use. Hearing aid(s) contains identification data, so that the control device can obtain the ID from the hearing aid(s) and history of use of hearing aid,
- Command device is a device such as mobile computing devices (smart phone or similar) with means to connecting with hearing aid and providing command data and audio data. Command device provides means to perform paired comparison procedure: to run the related software application, to present audio and visual signals and to collect response from the user, for example through a touch screen or similar human-machine-interface. The control device provides means to connect to remote centralized server and access a database and centralized software. Connection can be through the Internet or similar network, and
- Centralized server provides a means to host a database containing entries related with hearing loss. Entries relate to users of the procedure: age, sex and questionnaire data and individual outcomes of procedure. Centralized server runs a software application to process the database and computes the data requested by the command device.

II.1.1 Optional Details of the Invention and General Background of Paired Comparison Involving Probability of Preference:

To avoid comprehensive search in the large parameter space a method of probabilistic inference is employed. This method is based on the assumption that the parameter space is superimposed with a probability of psychological preference. According to Bayes' inference model, a data collected from the user is used to refine the probability of psychological preference. During this inference process, the peak of preference probability is defined that indicates the position of optimal parameter vector.

The concept of mapping of physical variables to psychological value is introduced by Thurstone, and described in [Thu 1959]. A general paired comparison model in connection with Bayes inference is introduced by Bradley and Terry [Brad 1952]. The particular algorithm used in our paired comparison procedure is described in [Chu 2005] and [Bro 2008]

Using the Bayes' methods the comprehensive search can be shortened by assuming a hypothesis for the probability of the preference called prior. The data collected in subsequent test is used to refine the prior resulting in posterior.

Instead of involving all possible parameter vectors—a limited set of data is used to statistically support the assumption about the underlying probability of preference.

The Bayesian framework introduces prior assumption about such preference of probability, called prior. This presents a hypothesis. Each set of collected data about preferences can be used to calculate improved assumption, called posterior. This relation is described in the simplified Bayes' rule:

$$\text{posterior} \propto \text{likelihood(data) prior}$$

or $$p(\theta|\text{data}) \propto p(\text{data}|\theta)p(\theta).$$

Where $p(\theta|\text{data})$ is posterior, the refined assumption after collecting the data; $p(\text{data}|\theta)$ is likelihood and represents a measure of plausibility of the newly collected data—assuming the prior; and $p(\theta)$ is prior—the initial assumption about the probability of preference. It is important to notice that the hyperparameter not only represents the physical variables of the presented acoustical stimuli but also the parameters of the model of latent functions involved in process preference generation. For detailed description refer to books on Bayes' inference.

The important connotation of this simplified Bayes' rule is that every new data (preference responses in this case) leads to improved assumption about the preference probability. The peak of improved 'posterior' probability indicates the "best fit" parameter vector. In this case the "best fit" does not have to be involved in any of the paired comparisons—it is inferred from the available data and the assumption.

Therefore, the rapidness and quality of the paired comparison fitting can be improved by following factors:
  Optimal selection of physical parameters to be involved in procedure
  Optimal initial assumption of the probability, the prior, and
  Optimal selection of the training set (pairs) to be presented to the user.

Improvements related to those factors are subject of the presented invention.

II.1.1.1 Optimal Selection of Physical Parameters to be Involved in Procedure

Fitting procedure for hearing aid is closely related to matching the individual hearing loss. Conventional fitting procedure consists of a.) diagnostic part—determination of hearing thresholds at different frequencies, presented in an audiogram and b.) calculating and applying in a hearing aid a prescription. Prescription is a vector of physical parameters, such as gain of acoustical amplification, used to configure signal processing in the hearing aid. The relation between audiogram and prescription is established by fitting rule—a prescriptive formula that uniquely calculates parameters for given audiogram (with some respect to age, sex and experience data). Very commonly used prescriptive formula is NAL-NL2 by Australian National Laboratory.

Prescriptive formulas are developed using sophisticated models and are statistically optimized using large population data. Therefore the formulas are capable to generate a complex prescription starting with limited data. In other words, the input of NAL-NL2 has less dimensions than its output.

This circumstance can be exploited in the present invention:

Fitting of a 12-channel hearing aid requires several physical parameters for each of the channels, where channel represents a processing in a limited part of frequency range. Frequency range is usually 200 Hz to 8 kHz, channels can be centred on frequencies of 250 Hz, 500 Hz, 1 kHz, 2 kHz, 4 kHz and so on. In a particular case the signal processing involved in fitting relate to WDRC or wide dynamic range compression. WDRC requires separate parameters for at least Gain, Compression ratio, Compression threshold. Each of those parameters represent one dimension of the parameter space and the 12 channels represent additional dimensions—resulting in a very large space impractical for any comprehensive search.

If a prescription rule such as NAL-NL2 is used to map an audiogram space to space of signal processing parameters, a significant reduction in dimensionality can be achieved. In one example, an audiogram can be sufficiently specified by hearing thresholds at following five frequencies: 0.5 kHz, 1 kHz, 2 kHz, 4 kHz, 6 kHz. In each of those points only one parameter is to be determined—absolute threshold (or hearing loss in dB). Assuming a constraint of the hearing aid to provide magnitude resolution of HL in 10 steps, then the total number of vectors in audiogram space is $10^5=100\ 000$.

In present provision a space of parameters is varied depending on targeted application or product. One targeted application is use in hearing aids sold Over-the-Counter, that means without involvement of trained professionals in fitting. Such hearing aids might be subject to regulations that limit the maximal acoustical amplification and/or acoustical output. For that reasons, only a limited portion of audiogram space will be eligible for search. In one particular example the hearing aid can be designed to cover only slight and mild hearing loss. Slight and mild hearing loss is specified with audiogram values between 16 dB and 40 dB [Ash 2017]. If the attempted resolution of audiogram search in this application is 4 dB, and each audiogram frequency will have 6 possible HL values (20 dB, 24 dB, . . . , 40 dB), then the total number of discrete points in audiogram space is $6^5=7\ 776$, which is a significant reduction, compared with the space of all possible audiograms related to human hearing.

II.1.1.2 Optimal Initial Assumption of the Probability, the Prior

Sensorineural hearing loss is individual, however certain types of hearing loss are statistically more probable. Age-related and noise-induced hearing loss affect predominantly high frequencies. They also progress with time—with progressing age or with prolonged exposure to noise. It is therefore possible to obtain statistical correlation of hearing loss with age, gender and particular manifestations of hearing loss. The most important particular manifestations of hearing loss relate to difficulties in understanding speech. Reported difficulties in understanding speech are an indication of hearing loss, a circumstance that can be used in calculating a probability that a person belongs to some of the population categories that are correlated with a specific type of hearing loss.

An example of statistical data about correlation between age, gender and hearing loss can be found in [Sun 2010].

Collecting data about age, sex from the customer and additionally collecting a response about progress of hearing loss indicators (such as speech understanding problems) can be used for categorizing the user into one of the demographic categories that are correlated with a particular hearing loss. For example a male user aged 60 and who reports a significant decline in speech understanding in last 5 years can be statistically most likely to experience a 15 dB increase of hearing thresholds at frequency of 2 kHz and 30 dB increase at 4 kHz.

While those figures could be a very inappropriate guess to precisely predict the actual hearing loss, they can be a very helpful starting point for paired comparison procedure. In other words, they serve as a Bayesian hypothesis to be corrected as the preference data is collected.

A Prior for the Bayesian inference in audiogram space is not only represented by the statistically obtained average audiogram for particular demographic category. In addition, the prior involve the model of probability that one stimulus (representing a point in audiogram space) will be preferred to another. Psychological response to a pair presented stimuli, a decision which stimulus is preferred, is guided by latent, non-observable, functions. Those functions are described by a covariance matrix containing covariances between latent functions related to two different audiograms. The covariances are usually modeled using Gaussian kernel function. For detailed description of modeling the prior see [Chu 2005].

The correlation between user's data input and the audiogram prior is stored in a database. This database resides in a centralized server and is regularly updated as new users complete the paired comparison procedure. Control device will for that reason connect to remote server and request the prior data for given user input. A software application residing on the centralized server will evaluate the prior for the request and return it to the control device.

Using Hearing Loss Diagnosis from a Personal Health Record as a Prior

Personal diagnostic data (Audiogram or comparable audiometric results) are in some cases available to the control device before the fitting of the hearing aid. This data can be used to calculate amplification prescription immediately and configure signal processing in a hearing aid. However, this diagnostic data can be dated and, or a fine-tuning (in addition to a immediately calculated fit) of hearing aid can be beneficial. In those cases a paired comparison procedure can be performed with the diagnostic data used as prior.

Personal diagnostic data can be obtained in control device from following origins: a.) accessing a remote database that stores healthcare data, for example a data of healthcare provider b.) use diagnostic data obtained through an hearing test application, residing on control device (such as hearing test apps on smart phones) or c.) a record from a personal Health record such as Health Data app provided by iOS operating system, d.) audiometric data imported to control device using human interface, such as typing, or any other similar origin.

Following any of those initial quantifications of individual hearing loss, the prior is available as a multidimensional probability density function (pdf). The dimensions of this pdf relate to audiogram points (elevations of absolute thresholds at different frequencies) and parameters thereof.

II.1.1.3 Optimal Selection of the Test Data

Not the whole parameter space is of interest for a particular user, and therefore the search can be optimized if it is performed in the area of most interest. This means that the sparse data will be compared instead of full space. The area of interest coincide with the area of higher preference probability, so the samples should originate from this area.

If the pairs are selected such that the parameter vectors are very close to each other, the decision will be affected by discriminable dispersion. The resulting decision will provide little significance and will also increase the cognitive load to the user. But in the search procedures, as the parameter converge to the optimal point, the difference becomes less and less distinguishable.

The success of the paired comparison method depends heavily on the choice of parameter-vector pairs that are used in production of stimuli. The proposed method optimizes this choice by sampling from the prior pdf. In doing so the vectors associated with high probability of preference will be used more frequently than those outside of this subset.

Sampling from the pdf is made according to one of the known sampling methods such as those presented in [Bis 2009]. Additionally, if the tails of pdf become thin, an alternative pdf can be used to avoid ignoring of test data outside of a very narrow area. Then method of importance sampling can be employed to assign contribution weights to the stimuli and related decisions, depending on the difference between pdfs. [Bis 2009].

One method to take into consideration the previously tested data and test the most promising is related to Thompson sampling. In this case a trade-off between exploration (preferring area not tested yet) and exploitation (preferring areas close to the optimal data from previous tests) is made. An acquisition function is used to find most optimal candidates.

Narrowing of area of search is beneficial for reduction of duration of the procedure. The proposed method therefore introduces sequential update of the prior. In each stage a number of tests is performed and the calculation of posterior constitutes a new hypothesis about the preference of the user. In general, we assume that the posterior will be a more precise description of the preference of the user. Therefore the next stage of paired comparisons can be performed with test pairs sampled from a more informative prior.

After each stage, the confidence of the resulting pdf can be assessed. If the confidence in the obtained pdf increases above pre-determined threshold, the procedure can be interrupted and the result be used as best-fit.

III. BRIEF DESCRIPTION OF THE DRAWINGS

Figure 2:
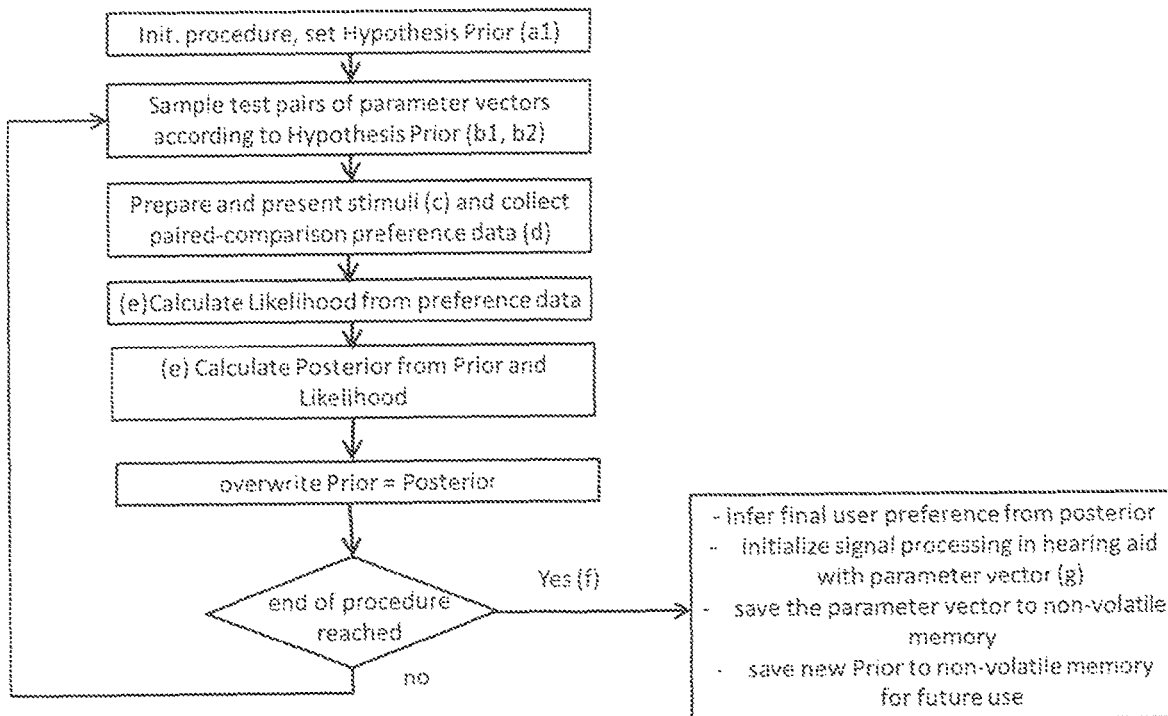
Figure 3:
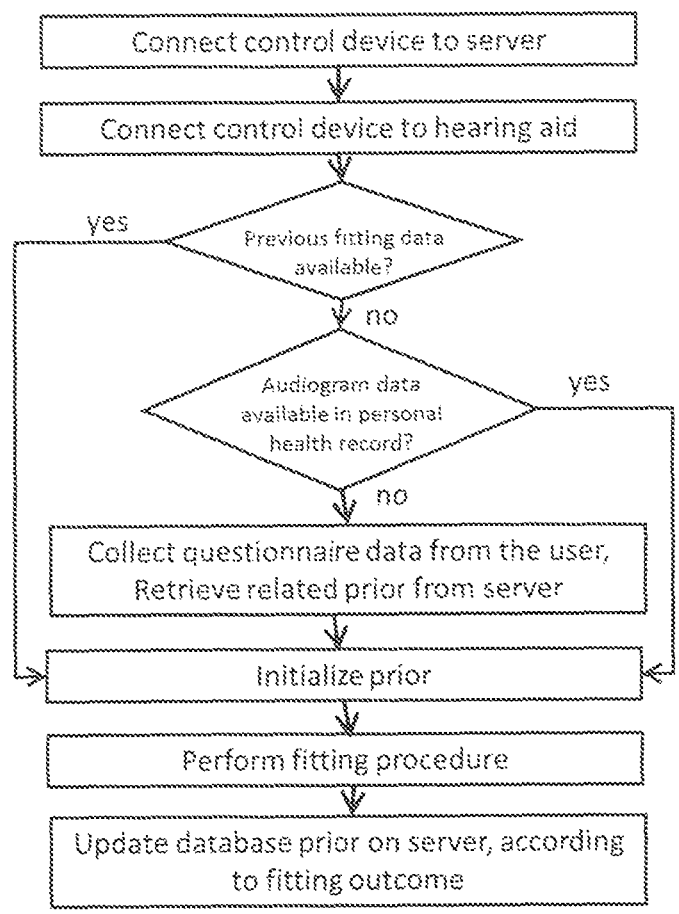

In the following, in order to further demonstrate the present invention, illustrative and non-restrictive embodiments are discussed, as shown in the drawings, which show:

FIG. 1 a schematic view of a hearing aid configuration system according to the invention, FIG. 2 a schematic view of the method according to the invention, and FIG. 3 another schematic view of an embodiment of the method according to the invention focusing on the server interactions for paired comparison procedure.

IV. DETAILED DESCRIPTION OF EMBODIMENTS OF THE INVENTION

In the following figures similar reference signs refer to similar features unless expressly depicted otherwise.

FIG. 1 shows a schematic view of a hearing aid configuration system 1 for carrying out the method according to the invention, said system comprising at least one hearing aid 2 to be configured, at least one external configuration unit 3 for communicating with the at least one hearing aid 2, and at least one computer-readable storage medium 4 comprising a program logic for carrying out the method according to the invention. The external configuration unit 3 is configured to access a the computer-readable storage medium 4. In this embodiment, the configuration unit 3 comprises the computer-readable storage medium 4.

A remote server 5 is connected to the external configuration unit 3 providing a database of user records.

FIG. 2 shows a schematic view of the method according to the invention. Therein, an exemplary embodiment of the method for enhancing the configuration of a hearing aid device 2 (see FIG. 1) of a user is shown, said method using an external configuration unit 3 accessing a database of previously known user records, wherein the hearing aid device 2 is arranged to be configured according to an individual set of configuration parameters (for instance gain, compression ratio, compression threshold, each parameter adjustable within a certain resolution and for a certain frequency band), said method comprising the following steps:

a) receiving user description data, said description data comprising previously known data (for instance age, gender, prior settings (history), diagnostic application, health record) about the user, a1) matching the user description data with the database of previously known user records in order to derive (initial) user preference description data b) using the user preference description data to derive
  b1) an assumed set of preferred configuration parameters (preferably a reduced set of configuration parameters), and
  b2) an assumed set of preferred values for the assumed set of preferred configuration parameters, optional b3) setting the remaining parameters to a default value,
  said parameters and its values according to steps b1) and b2) (and optional b3) being determined based on an estimation of their likelihood of matching the users preference description data, c) preparing at least two different sound samples based on a pre-defined set of samples and the parameters and its values derived in step b) and presenting the at least two prepared different sound samples to the user, d) receiving a user selection relating the preferred one of the at least two sound samples via the external configuration unit 3, e) combining the result of the selection into a new user preference description data, said new user preference data being merged with the user preference description data of step b) and iteratively repeating steps b) to e) until a pre-definable success condition is reached, f) yielding a final set of configuration parameters and its values, and g) configuring the hearing aid device 2 according to the final set of configuration parameters and its values.

In the following, one more detailed but still schematic embodiment of the invention will be described in detail with reference to FIGS. 1 to 3. Without loss of generality this embodiment uses Bayes' theorem to update the assumption about the best fitting parameter set according to prior hypothesis and user preference related to two presented stimuli. The actual and exemplary calculations related to obtaining the posterior from the Bayes' formula are known and sufficiently described in [Chu 2005] and [Bro 2008]. Without loss of generality only a single hearing aid device 2 is fitted in the described procedure, fitting of binaural devices is based on same principles by involving the rules for binaural amplification known from audiology. Without loss of generality only a limited number of signal processing parameters and user data are involved in the following example. The choice of involved parameters will depend of particular product and its use-case. If the product is intended for compensation of mild hearing loss of a first-time user of a hearing aid, fitting of few parameters related to amplification will be sufficient, if the use-case is fine-tuning of clinically fitted hearing aid device 2, then the choice and number of parameters will be different.

The procedure of fitting a hearing aid 2 according to the proposed invention can comprise the following steps (the step descriptions with regard to FIG. 2 correlating with the steps of claim 1):

1. User starts the procedure by placing a hearing aid device 2 in wearing position on one of his ears. Devices incorporating the means for wireless connection according to Bluetooth standard are turned on and are operating. The user starts the application on the configuration device (i.e. external configuration unit 3), for example a smart-phone, incorporating the means for wireless connection using Bluetooth standard. The configuration device 3 also incorporates means for connecting to remote server 5 through the Internet, for example by using wireless network access. The application establishes Bluetooth Low Energy communication with the hearing aid device 2 and exchanges the validation data, confirming that the hearing aid device 2 is compatible with the application.

2. The user is asked by the application to fill in his personal data: age and sex. The interaction of the application with the user is maintained through the graphical user interface (GUI) consisting of forms for alphanumerical entry, radio buttons or menus. Use of GUI can be supported by written, spoken or video instructions.

The particular user in the example is female of age 65. After collecting this user data, the application connects through the Internet to the remote server 5, containing database with statistically obtained user preference data. For the known user data, age and sex, the initial user preference data is obtained from the database in the form of probability of audiogram. (Step a1) in FIG. 2). The database contains statistical data with correlation of known user data: age and sex on one side and the probability of preference for hearing aid device 2 parameters on the other side. The statistics used in this database is compiled from the previous sessions and is updated with every new successful completion of the procedure.

3. The probability of audiogram from the database is used as a hypothetical starting point of the learning algorithm. Or in terms of Bayesian inference it is the Prior. Each hearing threshold at particular frequency points is in this case assumed to be distributed according to Gaussian distribution. The initial mean values of the hearing thresholds for the frequency vector f={500 Hz, 1 kHz, 2 kHz, 4 kHz} are HL_0={20, 21, 20, 30} respectively, expressed in dB HL (Hearing Loss) and the standard deviations are SD_0={0.32, 0.36, 0.4, 0.56} respectively.

4. From this initial user preference data, two audiograms are sampled in order to be used in preference comparison. (Step b1) and b2) in FIG. 2). Using sampling method such as Box-Muller [Bis 2009] and accepting only those sampled values that fall under the operating range of the given hearing aid, two sample audiograms are obtained:

HL1={21, 21, 20, 35} and HL2={23, 20, 22, 29}, expressed in dBHL. According to the audiograms HL1 and HL2 two sets of amplification parameters are calculated using NAL-NL1 rule, resulting in following values for Gain for 50 dB SPL inputs:

G50_1={5, 15, 16, 18} and G50_2={8, 15, 16, 15} expressed in dB REIG (real ear insertion gain), and compression ratios: CR1={1.21, 1.62, 1.69, 1.79} and CR2={1.3, 1.56, 1.74, 1.76}.

5. Speech samples representing sentences stored in the application are processed by signal processing routine in the application. (Step c) in FIG. 2). Signal processing routine implements WDRC and is configured with parameters G50_1 and CR1. All other parameters such as time-constants and compression threshold are hold fixed at the default value for this particular device. Using this configuration speech samples are processed into first presentation samples. The process is repeated for parameters G50_2 and CR2 producing second presentation samples.

6. Using Bluetooth connection, samples are streamed to the hearing aid device 2 and presented to the user avoiding any additional signal processing in the device. The user is asked by the application to provide preference for the first or second presentation samples. User selects second presentation sample. (Step d) in FIG. 2)

7. Considering the initial user preference data and considering the likelihood of the users preference selection, a new user preference data is calculated. In terms of Bayesian inference new preference data is the Posterior. This calculation can be made using Bayes' rule, a similar utilization is described in [Chu 2005]. The Bayes' inference involves the assumption about the kernel function and parameters that describe the search algorithm. Those parameters are subject of update in this step. New user preference data consists of updated mean values for audiogram HL_1 and updated standard deviations SL_1. Those are used for sampling new pair of sample parameters and producing new pair of presentation samples as in steps b1 and b2 in FIG. 2.

8. This process is iteratively repeated until one of the success criteria is achieved: Either the standard deviations of audiogram distribution fall below a prescribed threshold or the maximum number of iterations is reached. If the standard deviation of the preference falls below a specified limit, this means that the procedure resulted in convergence toward the most preferred set of parameters. If this sufficient convergence is not reached within maximum number of iterations, the result still can be valid. Maximum number of iterations is set to 20 in order to limit the duration of the procedure. In case the maximal number of iteration is achieved, the secondary criteria is tested to rule out that the procedure is not performed correctly. One possible secondary criteria relates to the progress of the iterative procedure and validates the procedure if the parameter set followed same tendency in most of the iterative steps.

9. At the end of procedure the winning set of parameters—final mean values for audiogram are used to configure the hearing aid device 2. (Step g) in FIG. 2). This is done by the application that controls the circuitry of the hearing aid device 2 through the Bluetooth connection. The winning set of parameters is also sent to the remote server, where dedicated software updates the database by including the winning set of parameters into statistical data.

Of course, the invention is not limited to the examples given in this specification. In particular the invention is not delimited to the precise values used in the exemplary calculations and equations, which merely show one embodiment of the invention that can be carried out by a person skilled in the art. In view of the disclosure of this application, a person skilled in the art is able to adjust the exemplary embodiments accordingly, in particular to set or modify the calculations and parameters described above. Accordingly, the characteristics described for a variants or embodiments may also be present in other variants or forms of use and can be combined with each other.

V. REFERENCES

[Ash 2017] http://www.asha.org/public/hearing/Degree-of-Hearing-Loss/

[Bis 2009] Bishop, Christopher—Pattern Recognition And Machine Learning—Springer 2006

[Brad 1952] R. A. Bradley, M. E. Terry, "The rank analysis of incomplete block designs. I. The method of paired comparisons" *Biometrika*, 39 (1952) pp. 324-345

[Bro 2008] Brochu Eric and Nando D. Freitas and Abhijeet Ghosh, Active Preference Learning with Discrete Choice Data, Advances in Neural Information Processing Systems 20, Curran Associates, Inc., (2008) pp. 409-416

[Chu 2005] Chu, W. and Ghahramani, Z. (2005) Preference Learning with Gaussian Processes

[Hof 2016] Hoffman H J, Dobie R A, Losonczy K G, Themann C L, Flamme G A. Declining Prevalence of Hearing Loss in US Adults Aged 20 to 69 Years. *JAMA Otolaryngol Head Neck Surg.* 2017; 143(3):274-285. doi: 10.1001/jamaoto.2016.3527

[Kuk 2002] Kuk F. K. (2002). Paired comparisons as a fine-tuning tool in hearing aid fittings. In Valente M, editor. (Ed.), Strategies for selecting and verifying hearing aid fittings (2nd ed., pp. 125-150). New York: Thieme

[Thu 1959] Thurstone, L. L. (1959). *The Measurement of Values*. Chicago: The University of Chicago Press.

[Sun 2010] Kim, Sunghee & Jung Lim, Eun & Soo Kim, Hak & Ho Park, Jun & Jarng, Soon & Heun Lee, Sang. (2010). Sex Differences in a Cross Sectional Study of Age-related Hearing Loss in Korean. Clinical and experimental otorhinolaryngology. 3. 27-31. 10.3342/ceo.2010.3.1.27.

The invention claimed is:

1. A method for enhancing the configuration of a hearing aid device of a user, said method using an external configuration unit accessing a database of previously known user records, wherein the hearing aid device is arranged to be configured according to an individual set of configuration parameters, said method comprising the following steps:

a) receiving user description data, said description data comprising previously known data about the user, wherein the user description data comprises the age and sex of the user;

a1) matching the user description data with the database of previously known user records in order to derive user preference description data that is obtained from the database in form of probability of an audiogram, wherein the database contains statistical data with correlation of previously known user data, namely age and sex on one side and a probability of preference for hearing aid device parameters on the other side, wherein the database of previously known user records is stored on a server and the external configuration unit is configured to connect to this server in order to access to the database or the database of previously known user records is locally stored on the external configuration unit, b) using the user preference description data to derive
   b1) an assumed set of preferred configuration parameters, and
   b2) an assumed set of preferred values for the assumed set of preferred configuration parameters,
   said parameters and its values according to steps b1) and b2) being determined based on an estimation of their likelihood of matching the users preference description data, wherein the preferred configuration parameters obtained in step b) are sampled dependence from their probability density function, wherein their probability density function is obtained from the user preference description data, c) preparing at least two different speech samples based on a pre-defined set of speech samples and the parameters and its values derived in step b) and presenting the at least two prepared different speech samples to the user, d) receiving a user selection relating the preferred one of the at least two speech samples via the external configuration unit, e) combining the result of the selection into a new user preference description data, said new user preference data being merged with the user preference description data of step b) and iteratively repeating steps b) to e) until a pre-definable success condition is reached, f) yielding a final set of configuration parameters and its values, and g) configuring the hearing aid device according to the final set of configuration parameters and its values.

2. The method according to claim 1, wherein the user description data additionally comprises at least comprises at least one of the following parameters: prior configuration data of the hearing aid device of the user and date of prior configuring data of the hearing aid device of the user; user preference data obtained in the prior session; data from diagnostic applications such as audiometric measurement of audiogram.

3. The method according to claim 1, wherein precisely two speech samples are presented in step c).

4. The method according to claim 1, wherein the parameters in step b) are obtained by applying an amplification-prescription formula, for instance NAL-NL2, to an audiogram with suitable likelihood to match the user preference data.

5. The method according to claim 1, wherein in step b) the assumed set of preferred configuration parameters is split into two groups, namely a first group of configuration parameters to be varied in step c), and a second group of configuration parameters which are set to an assumed default value and remain unvaried among the samples during step c).

6. The method according to claim 1, wherein the database of previously known user records is updated by the external configuration unit once a final set of configuration parameters and its values is determined according to step f), said final parameters and its values being added to the database.

7. The method according to claim 1, an initial set of configuration parameters comprises at least one of the following parameters: gain; compression ratio; compression threshold, attack-time constant, release-time constant, noise reduction level for at least one frequency band.

8. The method according to claim 7, wherein the initial set of configuration parameters comprise a number of frequency channels covering a bandwidth ranging from 100 Hz to 10 kHz, said bandwidth being split into the number of frequency channels, wherein the number is at least 3, preferably at least 5, most preferably between 5 and 32, wherein the configuration parameters of step b), in particular signal processing parameters such as gain or compression ratio, are set for each channel.

9. The method according to claim 1, wherein the external configuration unit (3) is a mobile phone, in particular a smart phone.

10. The method according to any of the preceding claims, wherein the pre-defined set of speech samples according to step c) is stored on the external configuration unit or on a server.

11. The method according to claim 1, wherein in step e) the new user preference description data is inferred from the previous user preference description data and the user selection according to Bayes' rule.

12. A hearing aid configuration system for carrying out the method according to claim 1, said system comprising
   at least one hearing aid device to be configured,
   at least one external configuration unit for communicating with the at least one hearing aid device, and
   at least one computer-readable storage medium comprising a program logic for carrying out the method according to any of the preceding claims,
   wherein said external configuration unit being configured to access the computer-readable storage medium.

* * * * *